(12) United States Patent
March

(10) Patent No.: US 7,653,424 B2
(45) Date of Patent: Jan. 26, 2010

(54) APPARATUS FOR MEASURING BLOOD GLUCOSE CONCENTRATIONS

(75) Inventor: Wayne Front March, New York, NY (US)

(73) Assignee: Eyesense AG, Basel (CH)

( * ) Notice: Subject to any disclaimer, the term of this patent is extended or adjusted under 35 U.S.C. 154(b) by 849 days.

(21) Appl. No.: 11/377,609

(22) Filed: Mar. 16, 2006

(65) Prior Publication Data

US 2006/0178572 A1  Aug. 10, 2006

Related U.S. Application Data

(63) Continuation of application No. 10/474,862, filed as application No. PCT/EP02/04647 on Apr. 26, 2002, now abandoned.

(60) Provisional application No. 60/287,053, filed on Apr. 27, 2001.

(51) Int. Cl.
   *A61B 5/1455* (2006.01)
(52) U.S. Cl. .................. 600/321; 600/316; 600/317
(58) Field of Classification Search .............. 600/310, 600/316, 317, 318, 319, 321, 322
   See application file for complete search history.

(56) References Cited

U.S. PATENT DOCUMENTS

| | | | |
|---|---|---|---|
| 3,731,681 A | | 5/1973 | Blackshe et al. |
| 3,925,178 A | | 12/1975 | Gesser et al. |
| 4,014,321 A | * | 3/1977 | March ....................... 600/319 |
| 4,099,859 A | | 7/1978 | Merrill |
| 4,143,949 A | | 3/1979 | Chen |
| 4,168,112 A | | 9/1979 | Ellis et al. |

(Continued)

FOREIGN PATENT DOCUMENTS

WO   WO-94/23284 A1   10/1994

(Continued)

OTHER PUBLICATIONS

E. De Berardinis et al., "The Chemical Composition of the Human Aqueous Humour in Normal and Pathological Conditions," Exp. Eye Res., 1965, 4, pp. 179-186.

(Continued)

*Primary Examiner*—Eric F Winakur
*Assistant Examiner*—Etsub D Berhanu
(74) *Attorney, Agent, or Firm*—Paul D. Strain; Fanelli, Strain & Haag, PLLC

(57) ABSTRACT

An apparatus for measuring ocular and/or blood glucose levels comprises
(a) an irradiating means (10) for irradiating light onto the eye (1) of a user from outside the cornea of the eye to excite an ocular glucose sensor in contact with an ocular fluid, said sensor being able to emit a total fluorescence having first and a second wavelength bands;
(b) an optical path splitting means (11) for splitting said total fluorescence into a first fluorescence and a second fluorescence, said first fluorescence and said second fluorescence traveling along first and second optical paths;
(c) a first detecting means (14) located in the first optical path;
(d) a second detecting means (17) located in the second optical path;
(e) a calculating means for calculating the intensity ratio of the first fluorescence to the second fluorescence and for determining an ocular glucose concentration in the ocular fluid; and
(f) an arithmetic means for converting the ocular glucose concentration into a blood glucose concentration.

10 Claims, 1 Drawing Sheet

U.S. PATENT DOCUMENTS

Figure 1:
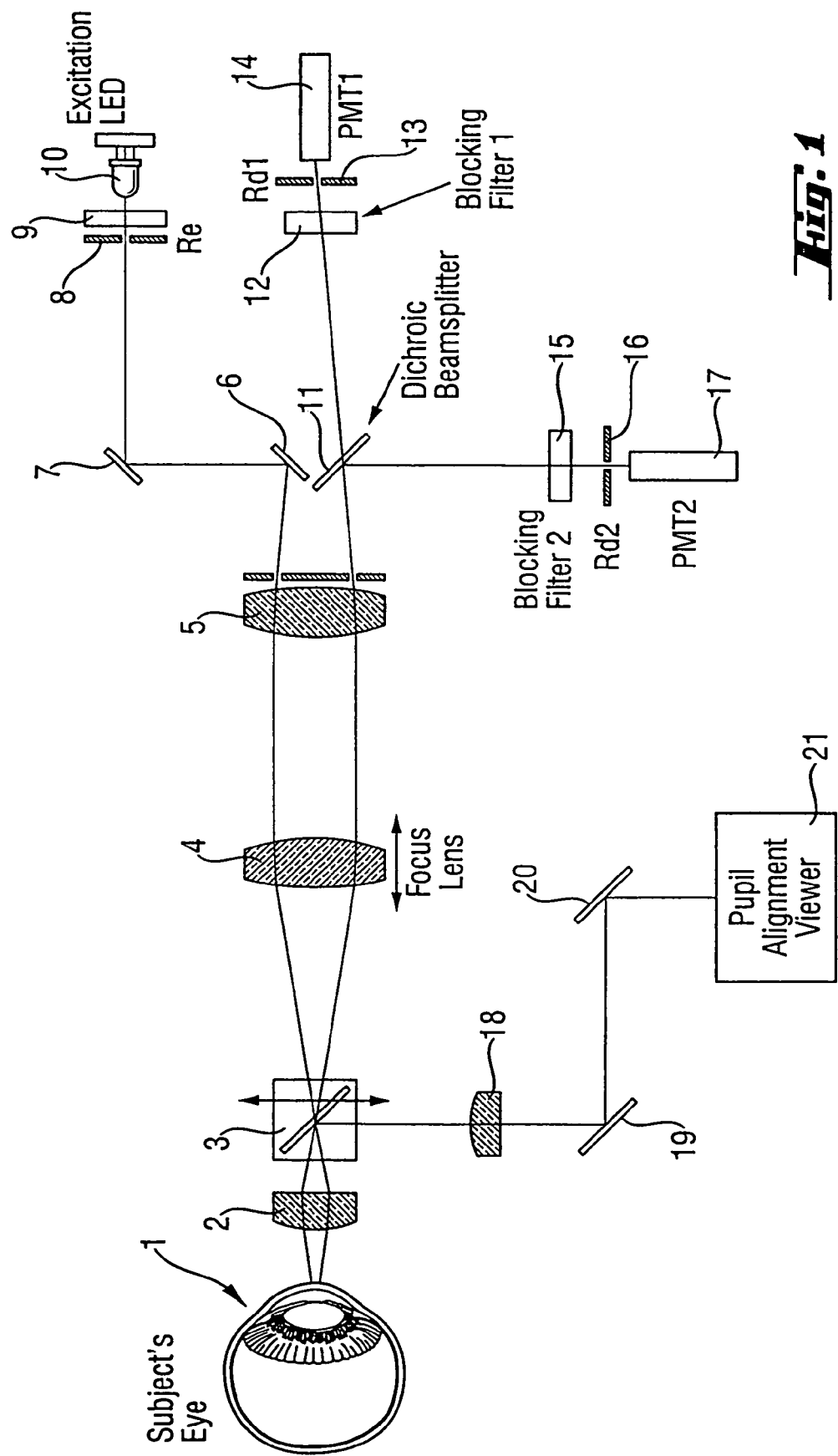

| | | | |
|---|---|---|---|
| 4,217,038 A | 8/1980 | Letter et al. | |
| 4,229,273 A | 10/1980 | Wajs | |
| 4,311,573 A | 1/1982 | Mayhan et al. | |
| 4,332,922 A | 6/1982 | Kossmehl et al. | |
| 4,388,164 A | 6/1983 | Moll et al. | |
| 4,409,258 A | 10/1983 | Feurer et al. | |
| 4,569,354 A | 2/1986 | Shapiro et al. | 128/665 |
| 4,573,994 A | 3/1986 | Fischell et al. | |
| 4,589,964 A | 5/1986 | Mayhan et al. | |
| 4,597,392 A * | 7/1986 | Opitz et al. | 600/321 |
| 4,799,931 A | 1/1989 | Lindstrom | |
| 4,923,375 A | 5/1990 | Ejlersen | |
| 5,007,928 A | 4/1991 | Okamura et al. | |
| 5,040,194 A | 8/1991 | Tjahjadi et al. | |
| 5,041,133 A | 8/1991 | Sayano et al. | |
| 5,071,432 A | 12/1991 | Baikoff | |
| 5,123,921 A | 6/1992 | Werblin et al. | |
| 5,127,901 A | 7/1992 | Odrich | |
| 5,277,872 A | 1/1994 | Bankert et al. | |
| 5,341,805 A | 8/1994 | Stavridi et al. | 128/633 |
| 5,400,114 A | 3/1995 | Yoshida et al. | |
| 5,426,158 A | 6/1995 | Mueller et al. | |
| 5,433,197 A | 7/1995 | Stark | |
| 5,476,511 A | 12/1995 | Gwon et al. | |
| 5,566,673 A | 10/1996 | Shiono et al. | |
| 5,609,640 A | 3/1997 | Johnson | |
| 5,762,836 A | 6/1998 | Bos et al. | |
| 5,776,381 A | 7/1998 | Haase | |
| 5,807,944 A | 9/1998 | Hirt et al. | |
| 5,820,557 A * | 10/1998 | Hattori et al. | 600/319 |
| 5,849,811 A | 12/1998 | Nicolson et al. | |
| 5,868,697 A | 2/1999 | Richter et al. | |
| 5,882,301 A * | 3/1999 | Yoshida | 600/318 |
| 5,894,002 A | 4/1999 | Boneberger et al. | |
| 5,957,890 A | 9/1999 | Mann et al. | |
| 5,965,631 A | 10/1999 | Nicolson et al. | |
| 5,984,961 A | 11/1999 | Macoul | |
| 6,040,194 A * | 3/2000 | Chick et al. | 436/501 |
| 6,051,025 A | 4/2000 | Ortuno et al. | |
| 6,088,606 A | 7/2000 | Ignotz et al. | 600/310 |
| 6,090,141 A | 7/2000 | Lindstrom | |
| 6,120,460 A | 9/2000 | Abreu | |
| 6,141,096 A | 10/2000 | Stern et al. | 356/318 |
| 6,181,957 B1 * | 1/2001 | Lambert et al. | 600/319 |
| 6,442,409 B1 * | 8/2002 | Peyman | 600/318 |
| 2001/0034500 A1 * | 10/2001 | March | 604/66 |

FOREIGN PATENT DOCUMENTS

| | | |
|---|---|---|
| WO | WO-99/35520 A1 | 7/1999 |
| WO | WO/ 00/33065 | 6/2000 |
| WO | WO-00/33065 A1 | 6/2000 |
| WO | WO 01/13783 A1 | 3/2001 |
| WO | WO-01/13783 A1 | 3/2001 |

OTHER PUBLICATIONS

R. Ballerstadt et al., "Competititve-binding assay method based on fluorescence quenching of ligands held in close proximity by a multivalent receptor," Analytica Chemica ACTA, vol. 345, 1997, pp. 203-212.

R.J. Russell et al., "A Fluorescence-Based Glucose Biosensor Using Concanavalin A and Dextran Encapsulated in a Poly(ethylele glycol) Hydrogel," Anal. Chem., vol. 71, No. 15, Aug. 1, 1999, pp. 3126-3132.

W. F. March et al., "Noninvasive Glucose Monitoring of the Aqueous Humor of the Eye: Part II. Animal Studies and the Scleral Lens," Diabetes Care, vol. 5, No. 3, May-Jun. 1982, pp. 259-265.

* cited by examiner

APPARATUS FOR MEASURING BLOOD GLUCOSE CONCENTRATIONS

This application is a continuation of U.S. patent application Ser. No. 10/474,862 filed on Mar. 26, 2004, now abandoned, which is a national stage filing under 35 U.S.C. 371 of International Application No. PCT/EP02/04647 filed Apr. 26, 2002, which claims benefit of U.S. Provisional Patent Application No. 60/287,053 filed Apr. 27, 2001.

The present invention provides an apparatus for measuring ocular and/or blood glucose levels, in particular by measuring fluorescence intensities simultaneously at two wavelengths. The apparatus is useful for accurately monitoring ocular and/or blood glucose levels.

One important aspect in the treatment of diabetes is the tight control of blood glucose levels, which requires frequent monitoring of blood glucose levels of patients so as to manage food intake and the dosage and timing of insulin injection. Currently, millions of diabetics are forced to draw blood daily to determine their blood sugar levels. To alleviate the constant discomfort and inconvenience of these individuals, substantial effort has been expanded in the search for a non-invasive or minimally invasive technology to accurately determine blood glucose levels.

Various non-invasive or minimally invasive technologies to measure blood glucose levels have been described. For example, WO-A-01/13783 discloses an ocular sensor for glucose that can be used to monitor blood glucose levels by determining glucose levels in an ocular fluid, such as tears, aqueous humor, or interstitial fluid. The ocular sensor disclosed by WO-A-01/13783 is an ophthalmic lens comprising a glucose receptor labeled with a first fluorescent label and a glucose competitor labeled with a second fluorescent label. The two fluorescent labels are selected in a way that while the competitor is bound to the receptor, the fluorescence of the second fluorescent label is quenched via a fluorescence resonance energy transfer. By monitoring change of the fluorescence intensity at a wavelength around the peak of the fluorescence of the second fluorescent label, the amount of the fluorescently labeled competitor that is displayed from the receptor by glucose is measured and provides a means of determining glucose concentration in an ocular fluid. This measurement can, in turn, be manipulated to provide a measurement of blood glucose level.

One of useful features of the method of WO-A-01/13783 for determining blood glucose levels using an ocular glucose sensor is that one of the two fluorescent labels could serve as an internal standard in the determination of glucose concentration in an ocular fluid and thereby could enhance the accuracy of determination of glucose concentration in an ocular fluid. The existence of an internal standard also could minimize the effects of positioning of the apparatus relative to the eye of a user on the reproducibility and accuracy of tests of blood glucose.

However, such feature can not be fully utilized, because currently available fluorophotometers are not capable of measuring simultaneously and accurately two fluorescence intensities at two different wavelengths. Accordingly, there is need for developing an affordable apparatus for accurately determining ocular glucose levels by measuring two fluorescence intensities at two different wavelengths and in turn for determining blood glucose levels.

Furthermore, like commercial in vitro (invasive) measurement instruments, i.e., those which require a drop of blood to measure blood glucose content, the accuracy and stability of an apparatus for measuring ocular glucose levels is needed to be verified periodically. Considering that most diabetic patients are not skilled in the art of fluorophotometer calibration, there is also need for developing methods and kits for calibrating an apparatus for measuring ocular glucose levels.

The present invention, in one aspect, provides an apparatus for measuring ocular and/or blood glucose levels. The apparatus of the invention comprises: (a) an irradiating means for irradiating light onto the eye of a user from outside the cornea of the eye to excite an ocular glucose sensor, wherein said ocular glucose sensor is in contact with an ocular fluid and can emit a total fluorescence having a first and a second wavelength bands upon irradiation with said irradiating means; (b) an optical path splitting means for splitting said total fluorescence having both bands into a first fluorescence having said first wavelength band and second fluorescence having said second wavelength band, wherein said first fluorescence travels along a first optical path and said second fluorescence travels along a second optical path; (c) a first detecting means located in the first optical path for detecting the intensity of the first fluorescence at a first wavelength; (d) a second detecting means located in the second optical path for detecting the intensity of the second fluorescence at a second wavelength; (e) a calculating means for calculating the intensity ratio of the first fluorescence to the second fluorescence and for determining based on the calculated intensity ratio an ocular glucose concentration in the ocular fluid of the user according to a predetermined calibration table or calibration curve; and (f) an arithmetic means for converting the ocular glucose concentration determined by the calculating means into a blood glucose concentration by referring to a predetermined correlation between blood glucose concentrations and ocular glucose concentrations. The present invention, in a further aspect, provides kits for calibrating an apparatus for measuring ocular glucose concentrations.

The term "ocular glucose concentration" as used herein refers to a glucose concentration in an ocular fluid.

The term "blood glucose concentration" as used herein refers to a glucose concentration in the blood stream of a person.

An ocular sensor is an ophthalmic lens comprising a glucose receptor labeled with a first fluorescent label and a glucose competitor labeled with a second fluorescent label. The two fluorescent labels are selected in a way that while the competitor is bound to the receptor, the fluorescence of one of two fluorescent labels is quenched via a fluorescence resonance energy transfer by the other fluorescent label. By monitoring change of the fluorescence intensity at a wavelength around the peak of the fluorescence of the quenchable fluorescent label, the amount of the fluorescently labeled competitor that is displayed from the receptor by glucose is measured and provides a means of determining glucose concentration in an ocular fluid.

Fluorescent labels, such as fluorescein, indocyanine green, malachite green, and rhodamine, which are quenched when the competitor moiety is bound but are unquenched when the competitor moiety is not bound, are preferred for use as quenchable fluorescent label in ocular glucose sensor.

The sensitivity of the ocular glucose sensor can be controlled by altering the concentration of the quenchable fluorescent label. Increasing the concentration of the quenchable fluorescent label in the ocular glucose sensor increases the range of fluorescence intensity and thereby increases the sensitivity of resulting measurements.

The glucose receptor moiety comprises a binding site for glucose. The binding site also binds a moiety that competes with glucose for binding and is therefore referred to herein as a "glucose/competitor moiety binding site". Binding of both the competitor moiety and glucose to the glucose/competitor moiety binding site is reversible. The receptor moiety can be antibodies, boronic acid, a genetically engineered bacterial fluoriprotein, or glucose oxidase, or preferably concanavalin A (Mansouri & Schultz, Bio/Tech 2:385 (1984)).

It is well known to a person skilled in the art to select a competitor moiety which will compete with glucose for binding to a glucose/competitor moiety binding site. For example, competitor moieties can be fluorescein dextran (which competes with glucose for binding to concanavalin A).

An ophthalmic lens can be removable lens, such as a contact lens, or a permanently implanted lens, such as an intraocular lens, a subconjunctival lens, or an intracorneal lens. Permanently implanted lenses are particularly well-suited for use in individuals who have compromised ocular function (e.g., cataracts) and also diabetic disease.

Ophthalmic lenses can be corrective lenses or can be constructed so that they do not affect visual acuity. Contact lenses optionally can comprise a tint and are preferably disposable, which reduces the risk of infection for the user. As used herein, the term "ophthalmic lens" may also refer to a shunt or implant that may rest in the cul de sac of the eye.

Ophthalmic lenses according to embodiments of the invention can be worn chronically to provide repeated measurements or can be worn for a single measurement. Both qualitative and quantitative measurements can be performed.

Construction of various types of ophthalmic lenses is well known in the art. Construction of contact lenses is taught, for example, in U.S. Pat. Nos. 5,965,631, 5,894,002, 5,849,811, 5,807,944, 5,776,381, 5,426,158, 4,099,859, 4,229,273, 4,168,112, 4,217,038, 4,409,258, 4,388,164, 4,332,922, 4,143,949, 4,311,573, 4,589,964, and 3,925,178.

Construction of intraocular lens implants is taught, inter alia, in U.S. Pat. Nos. 6,051,025, 5,868,697, 5,762,836, 5,609,640, 5,071,432, 5,041,133, and 5,007,928. Subconjunctival lenses are taught, for example, In U.S. Pat. Nos. 5,476,511, 5,400,114, and 5,127,901. Intracorneal lenses are taught, inter alia, in U.S. Pat. Nos. 6,090,141, 5,984,961, 5,123,921, and 4,799,931.

A variety of options are available for providing the receptor and competitor moieties in an ophthalmic lens. In one embodiment, the receptor moiety can be covalently bound to the ophthalmic lens material. In another embodiment, the ophthalmic lens comprises a polymer meshwork containing pores. The pores are of a size which permit the competitor moiety to bind reversibly to the glucose/competitor moiety binding site, but which prevent the receptor moiety and the competitor moiety from diffusing out of the ophthalmic lens. Suitable polymers for this purpose are known in the art and include hydrogels, such as stable polymers of polyethylene glycol hydrogel (PEGH), and modified polyvinylalcohol, such as nelfilcon A.

In another embodiment, the ophthalmic lens comprises a receptor moiety layer, a polyelectrolyte layer, and a competitor moiety layer. The polyelectrolyte layer includes one or more polyelectrolytes, which are generally high molecular weight polymers with multiple ionic or ionizable functional groups. At least one polyelectrolyte in the polyelectrolyte layer has a charge opposite to the overall charge of the receptor moiety and competitor moiety layers. Suitable polyelectrolytes include positively charged PDDA (polydiallyldimethyl-ammonium chloride) and negatively charged PAA (polyacrylic acid). Assembly of the layers is based upon sequential adsorption of oppositely charged polyions. The sensor and spacing polyelectrolytes are deposited as uniform thin films (1-10 nm) in 10-15 deposition cycles onto the porous polyvinyl alcohol or hydrogel matrix, resulting in only a 100-500 nm thick coating for the sensing film, which is highly biocompatible. A typical sequence for construction of an ophthalmic lens suitable for glucose detection involves a deposition cycle of ultrathin (1-10 nm) films of PDDA, PAA, PDDA, concanavalin A, PDDA, PAA, PDDA, fluorescein dextran, PDDA, PAA, PDDA, PAA, concanavalin A, PAA, fluorescein dextran, PAA, etc. Technology for constructing ophthalmic lenses comprising such layers is taught, for example, in WO-A-99/35520.

A calibration table or calibration curve as used herein means a table or curve containing in correlated form fluorescence intensity ratios and their corresponding actual glucose concentrations. A calibration table or calibration curve can be obtained once a day or just before testing of blood glucose levels by using at least three standard solutions with known glucose concentrations over a glucose concentration range from 0 to 500 mg/L. The obtained calibration table or curve is preferably stored in the apparatus which is used subsequently to determine blood glucose concentration.

Standard solutions can be provided to a user in calibration kits. They are stored in containers, preferably a rectangular having a plurality of separate compartments. The kits can also include calibration instruction.

The correlation between blood glucose concentration and ocular glucose concentration can be determined by methods well known in the art. See, for example, March et al., Diabetes Care 5, 259-65, 1982; Süllmann, in Handbuch der Physiologischen Chemie, Vol. II/a, p. 867 ff., Springer, Berlin, 1956; Graymore, in The Eye, Vol. I, p. 348, Davson, ed., Academic Press, NY, 1962; De Berardinis et al., Exp. Eye Res. 4, 179, 1965; Pohjola, Acta Ophthalmologica Suppl. 88, 1966; Reim et al., Ophthalmologica 154, 39-50, 1967; Kinsey & Reddy, in Prince, ed., The Rabbit and Eye Research, C. C. Thomas, Springfield, Ill., 1964, p. 218. It is preferably that such correlation between blood glucose concentration and ocular glucose concentration can be stored in the apparatus of the present invention so that the measurement of ocular glucose concentration can be converted into a value of blood glucose concentration.

FIG. 1 is a schematic view showing the construction of an apparatus for measuring ocular glucose concentrations according one embodiment of the invention. The apparatus includes convex lenses 2, 4 and 5, polarizer 3, mirrors 6, 7, 19, and 20, apertures 8, 13 and 16, light emitting diode 10 serving as irradiating means, a dichroic beamsplitter 11, two photomultiplier tubes (PMT) 14 and 17 serving as detecting means, filter 9, a pupil alignment viewer 21, a power supplier (not shown), a processing circuit (not shown) serving as both calculating and arithmetic means for determining ocular/blood glucose concentration, and a light-emitting display panel serving as means for displays blood glucose concentrations. The dichroic beamsplitter 11 is used to split the fluorescence from the eye 1 into a first fluorescence having a first wavelength band and a second fluorescence having a second wavelength band, so that the PMTs 14 and 17 can simultaneously measure the intensities of the first and second fluorescences at two different wavelengths. By observing on the pupil alignment viewer 21, with his or her own eye 1, the subject is capable of verifying that the excitation light emitted by the LED 10 is focused on the pupil of the eye via the convex lenses 2 and 18, mirrors 19 and 20, and polarizer 3.

The processing circuit obtains predetermined calibration table or curve of fluorescence intensity ratios and their corresponding actual glucose concentration and predetermined correlation between the blood glucose concentration and ocular glucose concentration. The measured blood glucose value is displayed on the light-emitting display panel. Further, the measured blood glucose concentration value may be transmitted to another piece of equipment via wire or cable, or wirelessly, such as via radio frequency or infrared transmission. A telemetry signal can be transmitted to an infusion pump, which can provide insulin to maintain suitable levels of glucose in the body. The telemetry signal may be analog or digital.

Infusion pumps are well known in the art for delivering a selected medication to a patient including humans and other animals in accordance with an administration schedule which can be preselected or, in some instances, preprogrammed. Pumps for use in this invention can be worn externally or can be directly implanted into the body of a mammal, including a human, to deliver a specific insulin to the mammal in controlled doses over an extended period of time. Such pumps are well known and are described, for example, in U.S. Pat. Nos. 5,957,890, 4,923,375, 4,573,994, and 3,731,681. Further, the measured blood glucose concentration value may be transmitted to another piece of equipment via wire or cable, or wirelessly, such as via radio frequency or infrared transmission. A telemetry signal can be transmitted to an infusion pump, which can provide insulin to maintain suitable levels of glucose in the body. The telemetry signal may be analog or digital.

The apparatus of the invention can be a free-standing device, a table-top device, or a hand-held device. For convenience, the detector can be a miniaturized device and may be worn or carried as a personal accessory, for example, mounted in the frame of a pair of eye glasses.

In order to better enable the reader to understand specific embodiments and the advantages thereof, reference to the following non-limiting examples is suggested.

EXAMPLE 1

Construction of an Intraocular Glucose Sensor

A structurally stable polymer of polyethylene glycol hydrogel (PEGH, Shearwater Polymers, Inc.) is used to construct an intraocular glucose sensor. PEGH is immobilized in an intra-ocular lens (Alcon Laboratories, 6 mm circumference, 1 mm thickness). Chemically immobilized pendant tetramethylrhodamine isothiocyanate concanavalin A (TRITC-ConA, Sigma) is incorporated into the PEGH as the receptor moiety and fluorescein isothiocyanate dextran (FITC-dextran, Sigma) is incorporated as the competitor moiety by polymerization under UV light, as described by Ballerstadt & Schultz, Anal. Chim. Acta 345, 203-12, 1997, and Russell & Pishko, Anal. Chem. 71, 3126-32, 1999. While the FITC-dextran is bound to the TRITC-ConA, the FITC fluorescence is quenched via a fluorescence resonance energy transfer. Increased glucose concentration frees the FITC-dextran and results in fluorescence which is proportional to glucose concentration.

EXAMPLE 2

Implantation of an Intraocular Glucose Sensor In Vivo

The intraocular lens glucose sensor described in Example 1 is implanted into the anterior chamber of the eye of a living New Zealand rabbit with a blood glucose concentration of 112 mg %. The implant is visible as a bright spot of green fluorescence (518 nm) within the eye. Careful examination with a bio-microscope slit lamp shows no sign of toxicity, rejection, or any reaction 6 months after implantation.

EXAMPLE 3

An apparatus is constructed according to the scheme shown in FIG. 1 to measure fluorescence from both fluorescin (517 nm) and rhodamine (570 nm). The apparatus has two excitation sources, one for fluorescein and one for rhodamine. Two photomultiplier tubes are employed to maximize the sensing of the signal at two wavelengths (517 nm and 570 nm). Detection of fluorescence from the encapsulated intraocular glucose sensor implanted in a rabbit eye is tested. In addition, fluorescence changes in response to glucose addition (0-500 mg/dl) to the sensor (fluorescin-dextran bound to rhodamine-concanavalin) in solution are monitored by the apparatus and compared to data obtained using a conventional laboratory scanning fluorophotometer (SpexFluorolog).

The ocular implant in the rabbit emits green fluorescence at 517 nm when excited with blue light at 488 nm. With the glucose sensor in solution, emitted fluorescence intensity at 517 nm increases linearly with increasing glucose concentrations below 22 nM (400 mg/L), whether the fluorescence is recorded by the apparatus or the laboratory fluorophotmeters. After addition of 11 nM (200 mg/L) glucose, fluorescence at 517 nm emitted from solutions increases by more than 30% compared to glucose-free controls.

The invention claimed is:

1. An apparatus for measuring blood glucose levels, comprising:
   (a) an irradiating means for irradiating light onto the eye of a user from outside the cornea of the eye to excite an ocular glucose sensor, wherein said ocular glucose sensor is in contact with an ocular fluid and can emit a total fluorescence having a first and a second wavelength bands upon irradiation with said irradiating means;
   (b) an optical path splitting means for splitting said total fluorescence having both bands into a first fluorescence having said first wavelength band and second fluorescence having said second wavelength band, wherein said first fluorescence travels along a first optical path and said second fluorescence travels along a second optical path;
   (c) a first detecting means located in the first optical path for detecting the intensity of the first fluorescence at a first wavelength;
   (d) a second detecting means located in the second optical path for detecting the intensity of the second fluorescence at a second wavelength;
   (e) a calculating means for calculating the intensity ratio of the first fluorescence to the second fluorescence and for determining based on the calculated intensity ratio an ocular glucose concentration in the ocular fluid of the user according to a predetermined calibration table or calibration curve; and
   (f) an arithmetic means for converting the ocular glucose concentration determined by the calculating means into a blood glucose concentration by referring to a predetermined correlation between blood glucose concentrations and ocular glucose concentrations.

2. An apparatus of claim 1, further comprising a displaying means for visually displaying the blood glucose concentration determined by the arithmetic means.

3. An apparatus of claim 1, further comprising a transmitting means for transmitting a signal to a pump, wherein said signal contains instructions for the pump to inject an amount of insulin into a tissue of the user.

4. An apparatus according to claim 1, wherein said irradiating means emits a light of third and fourth wavelengths which are different.

5. An apparatus of claim 2, further comprising a transmitting means for transmitting a signal to a pump, wherein said signal contains instructions for the pump to inject an amount of insulin into a tissue of the user.

6. An apparatus according to claim 2, wherein said irradiating means emits a light of third and fourth wavelengths which are different.

7. An apparatus according to claim 3, wherein said irradiating means emits a light of third and fourth wavelengths which are different.

8. A kit comprising:
at least three solutions of known glucose concentrations which are different, and an apparatus, wherein the apparatus comprises (a) an irradiating means for irradiating light onto the eye of a user from outside the cornea of the eye to excite an ocular glucose sensor, wherein said ocular glucose sensor is in contact with an ocular fluid and can emit a total fluorescence having a first and a second wavelength bands upon irradiation with said irradiating means; (b) an optical path splitting means for splitting said total fluorescence having both bands into a first fluorescence having said first wavelength band and second fluorescence having said second wavelength band, wherein said first fluorescence travels along a first optical path and said second fluorescence travels along a second optical path; (c) a first detecting means located in the first optical path for detecting the intensity of the first fluorescence at a first wavelength; (d) a second detecting means located in the second optical path for detecting the intensity of the second fluorescence at a second wavelength; (e) a calculating means for calculating the intensity ratio of the first fluorescence to the second fluorescence and for determining based on the calculated intensity ratio an ocular glucose concentration in the ocular fluid of the user according to a predetermined calibration table or calibration curve; and (f) an arithmetic means for converting the ocular glucose concentration determined by the calculating means into a blood glucose concentration by referring to a predetermined correlation between blood glucose concentrations and ocular glucose concentrations.

9. A kit of claim 5, wherein said known glucose concentrations are evenly distributed over a concentration range from 0 to 500 mg/L.

10. A kit of claim 5, further comprising an instruction for calibrating the apparatus for measuring ocular glucose concentrations.

* * * * *